US009017069B2

(12) United States Patent
Boyden et al.

(10) Patent No.: US 9,017,069 B2
(45) Date of Patent: Apr. 28, 2015

(54) ORAL ILLUMINATION SYSTEMS AND METHODS

(71) Applicant: Elwha LLC, Bellevue, WA (US)

(72) Inventors: Edward S. Boyden, Chestnut Hill, MA (US); Alistair K. Chan, Bainbridge Island, WA (US); Roderick A. Hyde, Redmond, WA (US); Jordin T. Kare, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/893,136

(22) Filed: May 13, 2013

(65) Prior Publication Data

US 2014/0335464 A1 Nov. 13, 2014

(51) Int. Cl.
| | |
|---|---|
| *A61C 7/12* | (2006.01) |
| *A61B 5/00* | (2006.01) |
| *A61B 7/04* | (2006.01) |
| *A61C 1/08* | (2006.01) |
| *A61C 19/04* | (2006.01) |
| *A61C 7/08* | (2006.01) |
| *A61C 7/20* | (2006.01) |
| *A61C 7/16* | (2006.01) |
| *A61C 7/18* | (2006.01) |

(52) U.S. Cl.
CPC ............... *A61B 5/742* (2013.01); *A61B 5/486* (2013.01); *A61B 5/682* (2013.01); *A61B 7/04* (2013.01); *A61C 1/088* (2013.01); *A61C 19/04* (2013.01); *A61C 7/08* (2013.01); *A61C 7/20* (2013.01); *A61C 7/16* (2013.01); *A61C 7/18* (2013.01)

(58) Field of Classification Search
USPC ...................................... 433/2, 6, 8
See application file for complete search history.

(56) References Cited

U.S. PATENT DOCUMENTS

| | | | | |
|---|---|---|---|---|
| 4,382,780 | A | * | 5/1983 | Kurz .................................. 433/5 |
| 4,683,588 | A | * | 7/1987 | Goldberg ......................... 381/61 |
| 5,454,716 | A | | 10/1995 | Banerjee et al. |
| 5,522,847 | A | * | 6/1996 | Kalis et al. .................... 606/234 |
| 5,730,151 | A | | 3/1998 | Summer et al. |

(Continued)

FOREIGN PATENT DOCUMENTS

WO WO 2011/079166 A2 6/2011

OTHER PUBLICATIONS

Callejas, Zoraida et al., "Predicting user mental states in spoken dialogue systems", EURASIP Journal on Advances in Signal Processing, Jan. 6, 2011, 21 pages.

(Continued)

*Primary Examiner* — Ralph Lewis
(74) *Attorney, Agent, or Firm* — Foley & Lardner LLP

(57) ABSTRACT

An oral illumination apparatus configured for placement in a mouth. The oral illumination apparatus includes a housing configured to be coupled to a structure in the mouth. The housing including a processing circuit. The oral illumination apparatus further includes a sensor coupled to the housing and configured to detect a characteristic from within the mouth, wherein the sensor provides a feedback signal indicative of the characteristic to the processing circuit. The oral illumination apparatus includes a light source coupled to the housing and operatively coupled to the processing circuit. The oral illumination apparatus further includes a power source coupled to the housing. The processing circuit is configured to control the light source in response to the feedback signal.

24 Claims, 7 Drawing Sheets

(56) References Cited

U.S. PATENT DOCUMENTS

| | | | |
|---|---|---|---|
| 6,077,073 | A | 6/2000 | Jacob |
| 6,299,441 | B1 | 10/2001 | Novak |
| 6,470,200 | B2 * | 10/2002 | Walker et al. ............... 600/344 |
| 6,956,601 | B2 | 10/2005 | Squilla et al. |
| 7,223,270 | B2 | 5/2007 | Altshuler et al. |
| 7,223,281 | B2 | 5/2007 | Altshuler et al. |
| 7,331,784 | B2 | 2/2008 | Suzuki |
| 7,354,448 | B2 | 4/2008 | Altshuler et al. |
| 7,422,598 | B2 | 9/2008 | Altshuler et al. |
| 7,451,852 | B2 | 11/2008 | Stewart et al. |
| 7,467,946 | B2 | 12/2008 | Rizoiu et al. |
| 7,572,124 | B2 | 8/2009 | Cipolla et al. |
| 7,610,919 | B2 * | 11/2009 | Utley et al. ............... 131/270 |
| 7,675,429 | B2 | 3/2010 | Cernasov |
| 2003/0133364 | A1 | 7/2003 | Merk et al. |
| 2003/0136416 | A1 | 7/2003 | White |
| 2003/0171686 | A1 * | 9/2003 | Gannon ............... 600/532 |
| 2003/0232303 | A1 | 12/2003 | Black |
| 2004/0043349 | A1 | 3/2004 | Liao |
| 2004/0181166 | A1 | 9/2004 | Williford et al. |
| 2005/0113654 | A1 | 5/2005 | Weber et al. |
| 2006/0033809 | A1 | 2/2006 | Farley |
| 2006/0110700 | A1 | 5/2006 | Cipolla et al. |
| 2006/0155171 | A1 | 7/2006 | Yang |
| 2006/0166157 | A1 | 7/2006 | Rahman et al. |
| 2006/0281042 | A1 | 12/2006 | Rizoiu et al. |
| 2006/0287855 | A1 | 12/2006 | Cernasov |
| 2007/0009856 | A1 | 1/2007 | Jones et al. |
| 2007/0134615 | A1 | 6/2007 | Lovely |
| 2007/0231767 | A1 | 10/2007 | Sears et al. |
| 2007/0259310 | A1 | 11/2007 | Goodson et al. |
| 2007/0276455 | A1 | 11/2007 | Fiset |
| 2008/0058587 | A1 | 3/2008 | Boyden et al. |
| 2008/0233541 | A1 | 9/2008 | De Vreese et al. |
| 2009/0018720 | A1 | 1/2009 | Bernard |
| 2009/0056044 | A1 | 3/2009 | Rizoiu et al. |
| 2009/0068610 | A1 * | 3/2009 | Brezniak ............... 433/9 |
| 2009/0228081 | A1 | 9/2009 | Perez |
| 2009/0278980 | A1 | 11/2009 | Sato |
| 2010/0112623 | A1 | 5/2010 | Fujimoto |
| 2010/0129767 | A1 | 5/2010 | Fishburne, Jr. |
| 2010/0136498 | A1 | 6/2010 | Baughman |
| 2010/0151407 | A1 | 6/2010 | Rizoiu et al. |
| 2010/0290647 | A1 * | 11/2010 | Abolfathi et al. ............. 381/151 |
| 2010/0304324 | A1 | 12/2010 | Dragan et al. |
| 2011/0184319 | A1 | 7/2011 | Mack et al. |
| 2011/0195739 | A1 | 8/2011 | Deleus et al. |
| 2011/0205153 | A1 | 8/2011 | Ueda et al. |
| 2012/0172679 | A1 | 7/2012 | Logan et al. |
| 2014/0112556 | A1 | 4/2014 | Kalinli-Akbacak |

OTHER PUBLICATIONS

Jones, Colin, Japanese inventors light up the night with LED braces, NY Daily News, Jan. 25, 2011, 3 pages.

LED Braces, from ubergizmo.com (www.ubergizmo.com/2011/04/led-braces-only-in-japan/), retrieved on May 23, 2013, 3 pages.

LED teeth braces, led mouthpiece, flashing teeth braces, from dhgate.com (www.dhgate.com/100pcs.-1-lot-led-teeth-braces-led-mouthpice/pff8080812e325f55012e716f5a6668e8.html), retrieved on May 23, 2013, 12 pages.

Light Up Flashing Mouthpieces, from flashingblinkylights.com (www.flashingblinkylights.com/lightupflashingmouthpieces-p-1188.html), retrieved on May 23, 2013, 2 pages.

Universidad Carlos III de Madrid, from uc3m.es (www.uc3m.es/portal/page/portal/actualidad_cientifica/noticias/computer_system_emotional), retrieved on May 23, 2013, 1 page.

Definition of "wear"; Oxford Dictionaries; printed Sep. 9, 2014; 1 page; located at http://www.oxforddictionaries.com/us/definition/american_english/wear.

PCT International Search Report: International App. No. PCT/US2014/037676; Sep. 12, 2014; pp. 1-3.

* cited by examiner

US 9,017,069 B2

ORAL ILLUMINATION SYSTEMS AND METHODS

BACKGROUND

Many different types of dental devices are commonly worn by people for various purposes. For example, corrective dental braces or orthodontic braces are commonly secured onto a person's teeth and are used to reposition and properly align the teeth. The braces are typically used to help correct underbites, overbites, cross bites, crooked teeth, and other dental issues. Further, after braces are removed, it is common for people to wear permanent or removable dental retainers to maintain the position of teeth such that the teeth do not shift out of position. The dental devices are typically designed without non-dental use considerations. Such dental devices may be constructed of metal braces, plastic retainer bodies, and metal wires that are tensioned and bent to provide forces to the user's teeth.

SUMMARY

One exemplary embodiment relates to an oral illumination apparatus configured for placement in a mouth. The oral illumination apparatus includes a housing configured to be coupled to a structure in the mouth. The housing including a processing circuit. The oral illumination apparatus further includes a sensor coupled to the housing and configured to detect a characteristic from within the mouth, wherein the sensor provides a feedback signal indicative of the characteristic to the processing circuit. The oral illumination apparatus includes a light source coupled to the housing and operatively coupled to the processing circuit. The oral illumination apparatus further includes a power source coupled to the housing. The processing circuit is configured to control the light source in response to the feedback signal.

Another exemplary embodiment relates to an oral illumination apparatus configured for placement in a mouth. The oral illumination apparatus includes a housing configured to be coupled to a structure in the mouth. The housing including a processing circuit. The oral illumination apparatus further includes a wireless receiver coupled to the housing and operatively coupled to the processing circuit. The oral illumination apparatus includes a light source coupled to the housing and operatively coupled to the processing circuit. The oral illumination apparatus further includes a power source coupled to the housing. The processing circuit is configured to control the light source in response to an instruction received through the wireless receiver.

Yet another exemplary embodiment relates to a method of controlling a light source of an oral illumination device worn in a mouth of a user, wherein the oral illumination device includes a processor and memory. The method includes detecting a characteristic from within the mouth through a sensor of the oral illumination device. The method further includes executing a lighting program by the processor in response to detecting the characteristic. The method includes controlling the light source in accordance to the lighting program.

Still another exemplary embodiment relates to a method of controlling a light source of an oral illumination device worn in a mouth of a user, wherein the oral illumination device includes a processor and memory. The method includes receiving an instruction from an external device through a wireless receiver of the oral illumination device. The method further includes executing a lighting pattern by the processor in response to the instruction. The method includes selectively controlling the light source in accordance to the lighting pattern.

An exemplary embodiment relates to an oral illumination apparatus configured for placement in a mouth. The oral illumination apparatus includes a body configured to be coupled to a plurality of teeth in the mouth and configured to at least partially cover the plurality of teeth. The oral illumination apparatus further includes a controller coupled to the body. The oral illumination apparatus includes a sensor coupled to the body and configured to detect a characteristic from within the mouth, where the sensor provides a feedback signal indicative of the characteristic to the controller. The oral illumination apparatus further includes a display coupled to the body and operatively coupled to the controller. The display is configured to display an image across at least one of the plurality of teeth. The oral illumination apparatus includes a power source configured to provide electrical power to the controller and the display. The controller is configured to instruct the display to display an image in response to the feedback signal.

DETAILED DESCRIPTION OF THE PREFERRED EMBODIMENTS

Figure 1A:
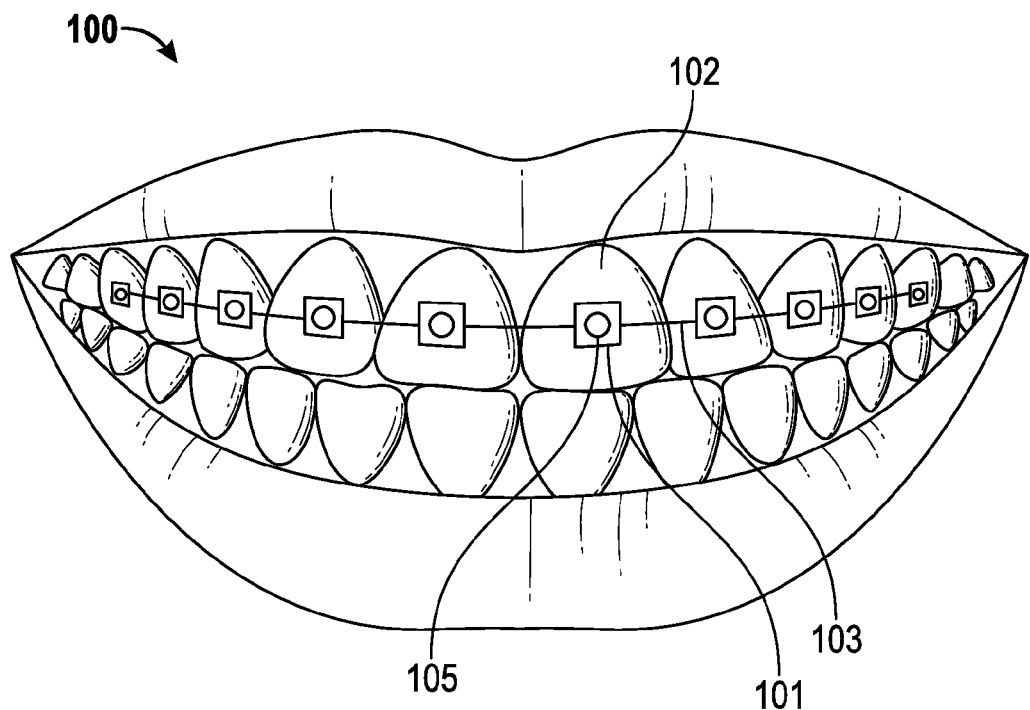
FIG. 1A is a schematic view of an illuminated dental braces system according to an exemplary embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to FIG. 1A, a schematic view of an illuminated dental braces system 100 is provided according to an exemplary embodiment. System 100 includes at least one brace 101 mounted on teeth 102. Each brace 101 is connected to another brace 101 with wire 103. Braces 101 are typically attached to teeth 102 through a specialized dental glue. In an alternative arrangement, braces 101 are secured to teeth 102 with a metal ring that wraps around an individual tooth 102 in addition to the dental glue. Brace 101 includes light source 105. Light source 105 emits light under designated circumstances. Wire 103 may be positioned, bent, and tensioned to apply forces to braces 101 in order to move teeth 102 into a desired position.

Figure 1B:
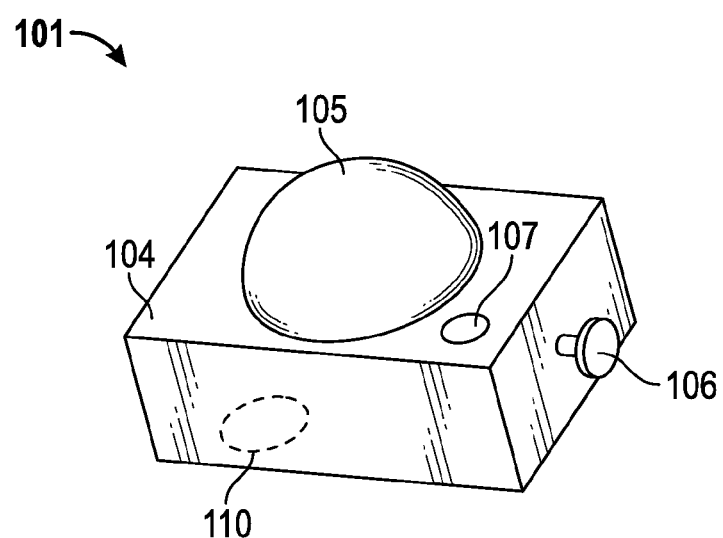
FIG. 1B is a perspective view of an illuminated brace according to the exemplary embodiment of FIG. 1A.

Referring to FIG. 1B, a perspective view of brace 101 is shown according to an exemplary embodiment. Brace 101 includes housing 104. Housing 104 contains various components of brace 101. Housing 104 may be made of stainless steel. The stainless steel may include titanium. Alternatively, housing 104 may be made of a ceramic or plastic. Housing 104 includes a top surface having light source 105. Light source 105 is mounted to the top surface. Alternatively, light source 105 is mounted within housing 104 and is visible through the top surface. Housing 104 includes a back surface configured for attaching to tooth 102. As discussed above, housing 104 may be attached to tooth with glue. Housing 104 may include a metal ring that encircles tooth 102.

Light source 105 is configured to emit light. Light source 105 may be any of a light emitting diode ("LED"), an organic LED ("OLED"), a light emitting semiconductor nanocrystal ("quantum dot"), an incandescent bulb, or any other light source. Light source 105 may include multiple light sources (e.g., an array of LEDs, an array of OLEDs, an array of quantum dots, etc.). In an alternate configuration, light source 105 is a display (e.g., an LCD display, an LED display, an OLED display, etc.) configured to emit light and/or display an image, a text character, or a symbol. Light source 105 may be configured to emit only a single color of light. Alternatively, light source 105 may be color adjustable such that the color of light emitted by light source 105 is selectable (e.g., white, blue, red, yellow, green, etc.). In another alternate configuration, light source 105 may be capable of emitting multiple different colors of light at the same time. In another alternate configuration, brace 101 comprises multiple housings 104, different ones of which emit different colors. In yet another alternative configuration, light source 105 may emit ultraviolet light. Light source 105 may be intensity adjustable such that the intensity of emitted light (i.e., the brightness level of light source 105) is adjustable.

In an exemplary embodiment, brace 101 includes wire connector 106. Wire connector 106 is configured to attach wire 103 to brace 101. Wire connector 106 is made of conductive metal. Wire connector 106 may be further configured to serve as an electrical contact such that a first brace 101 can utilize wire 103 to transmit or receive signals and/or electric current to or from a second brace. Accordingly, in an arrangement including multiple braces, each brace 101 can communicate and/or share electrical power with other braces through wire 103. In an alternative embodiment, housing 104 is configured to allow wire 103 to pass through or around brace 101 such that a single piece of wire 103 can connect multiple braces.

In an exemplary embodiment, brace 101 includes sensor 107. Sensor 107 is configured to detect a characteristic or condition from its placement within the user's mouth. Sensor 107 can detect a characteristic or condition within the user's mouth or outside of the user's mouth. In one configuration, sensor 107 is a bacteria sensor configured to detect the bacteria level in the user's mouth. Sensor 107 outputs a feedback signal to processing circuit 110. Processing circuit 110 may control (e.g., activate, deactivate, adjust brightness, adjust color, etc.) light source 105 based on the detected level of bacteria. In the event the detected level of bacteria exceeds a threshold level, light source 105 is either activated or deactivated depending on user programming. The activated light may be an ultraviolet light (to kill the bacteria) or a colored light (to alert the wearer or another that the wearer should brush his or her teeth). In an alternate configuration, sensor 107 is an ambient light sensor. In such a configuration, light source 105 is activated or deactivated based on the detected light level. Further, the level of light output by light source 105 (i.e., the brightness of light source 105) can be adjusted based on the detected ambient light level. For example, in dark ambient light situations (low light level situation), light source 105 may emit a lower intensity of light as it will be more easily visible; whereas in bright ambient light situations (high light level situation), light source 105 may emit light at a higher intensity. In certain situations where the ambient light exceeds a high threshold value (e.g., a very high light level situation), light source 105 may be instructed to not light at all as the light will not be easily visible even at a full brightness setting. Further, if the ambient light level falls below a threshold level of light, processing circuit 110 may determine that the user's mouth is closed, in which case light source 105 is turned on or off based on the programming. In yet another alternate configuration, sensor 107 is an optical sensor configured to detect a lighting pattern emitted from a device external to the user's mouth. In another alternate configuration, sensor 107 is a microphone. In such a configuration, light source 105 may be activated, deactivated, and/or adjusted (e.g., in color or in brightness) based on detected sound levels (e.g., activating with a threshold noise level, increasing or decreasing intensity with increasing or decreasing noise level, changing color based on detected noise level, etc.) and/or detected sound patterns (e.g., voice recognition, music recognition, identified words, etc.). In another alternate configuration, sensor 107 is a movement sensor. In such a configuration, light source 105 may be activated, deactivated, and/or adjusted (e.g., in color, in brightness) based on detected movement thresholds and patterns. For example, light source 105 may be activated, deactivated, adjusted (in color or intensity) when a chewing motion is detected or when the jaw opens or closes. In another alternate configuration, sensor 107 is a chemical sensor configured to detect the presence and amount of designated chemicals within the mouth (e.g., capsaicin, fluoride, etc.). In yet another alternate configuration, brace 101 includes a sensor array having multiple sensors each configured to detect a different characteristic (e.g., bacteria level inside the user's mouth, an amount of ambient light, noise, jaw movement, etc.). In such a configuration, light source 105 is configured to activate, deactivate, and/or change an operating parameter (e.g., intensity or color) based on detected characteristics. For example, light source 105 may be activated to emit ultraviolet light when detected bacteria levels exceed a threshold amount and when the wearer's mouth is closed based on feedback from the sensor array.

In some arrangements, system 100 may include a chemical secretor. The chemical secretor may be built into each brace 101 or may be built into a non-lighted brace (e.g., a molar brace). Accordingly, brace 101 may include a chemical storage unit (e.g., a tank) and a secretion device (e.g., a sprayer, a nozzle, an outlet). Each brace 101 may include a plurality of secretion devices. The chemical may be any of an anti-bacterial agent, an anti-carcinogenic agent, an oral cleaner (e.g., mouthwash), a breath freshener (e.g., mint spray), or another suitable chemical. The chemical may be secreted from brace 101 in response to a detected bacteria level. For example, if sensor 107 indicates that the detected bacteria level is above a threshold level, the chemical secretor may be programmed to secrete a chemical or combination of chemicals to counter the high bacteria level (e.g., secrete an anti-bacterial agent, a breath freshener, a oral cleaner, or a combination thereof). The chemical secretor may be programmed to secrete the chemical only when the wearer's mouth is closed.

Figure 1C:
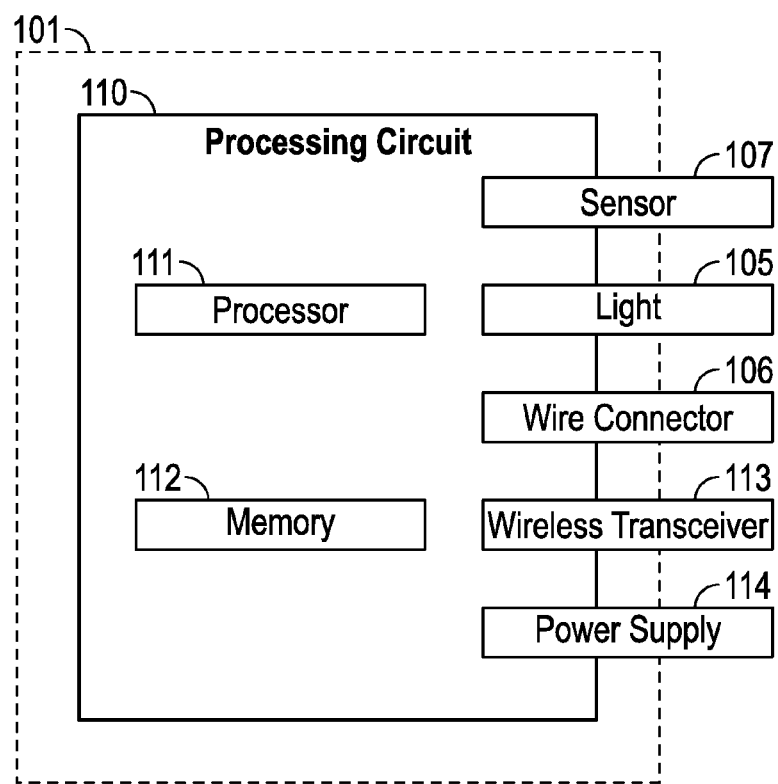
FIG. 1C is a block diagram of a processing circuit of the illuminated brace according to an exemplary embodiment.

In an exemplary embodiment, brace 101 includes processing circuit 110. Referring to FIG. 1C, a block diagram of processing circuit 110 is shown. Processing circuit 110 includes processor 111 and memory 112. Processing circuit 110 communicates with, and is operatively coupled to, light source 105, wire connector 106, sensor 107, and wireless transceiver 113. Processing circuit 110 is powered by power supply 114. Memory 112 stores necessary programming modules that, when executed by processor 111, control the operation of brace 101 (i.e., control the lighting of brace 101) based on desired user settings and output from sensor 107. For example, memory 112 may include a speech to text conversion module that, when executed by processor 111, converts detected audio patterns into text to be displayed by light source 105 (e.g., with a coded light pattern or as text characters and symbols displayed on light source 105). By way of further example, memory 112 may include a speech to text conversion module that, when executed by processor 111, identifies words within the detected audio patterns, compares them to one or more stored words, and controls the output of light source 105 based on the comparison, e.g., displaying specified light colors for selected key words. Accordingly, processor 111 is configured to control the output of light source 105, including activating and deactivating light source 105, changing a color of light source 105, changing a brightness level of light source 105, or changing a lighting pattern emitted from a plurality of light sources 105. A user may provide brace 101 settings through an external computing device (e.g., a laptop, a PDA, a smartphone, a tablet, etc.) in communication with processing circuit 110 through wireless transceiver 113. Wireless transceiver 113 is configured to receive and transmit data through a standard wireless networking protocol (e.g., Bluetooth, 802.11, 802.15, Wi-Fi, etc.). Alternatively, wireless transceiver 113 is configured to receive and transmit data through ultrasound or infrared communications. Processing circuit 110 is further configured to communicate with other braces. For example, brace 101 can communicate with a second brace such that each light source 105 activates, deactivates, or adjusts such that all lights on connected braces emit light at the same time or offset times, with the same or different intensities, and/or with the same or different colors to form patterns. Accordingly, brace 101 can communicate with other braces through wireless transceiver 113. Further, brace 101 can communicate with other braces through wire connector 106 and wire 103 (as discussed above, wire 103 can facilitate data and power transfer between connected braces). Processing circuit 110 is further configured to receive lighting instructions from external computing devices through wireless transceiver 113. The received instructions may include an on-demand lighting pattern to be executed by processor 111 upon receipt of the instruction (e.g., a lighting score) or a lighting pattern to be executed by the processor 111 upon the detection of a condition or characteristic.

Power supply 114 provides power to brace 101. Power supply 114 may receive power from any suitable source (e.g., a rechargeable battery, a non-rechargeable battery, etc.). In addition to a stand-alone power source such as a battery, power supply 114 may receive operating power and/or charge batteries from a wireless inductive power generator (i.e., by passing waves over coils that convert the electro-magnetic energy into electrical energy), by converting mechanical energy present during jaw movement into electrical energy through a mechanical energy converter, by converting solar energy into electrical energy through the use of a photovoltaic cell located on brace 101, and/or by chemically extracting electrical energy from food located within the user's mouth. Brace 101 is configured to transmit or receive power from power supply 114 to another brace through wire connector 106 and wire 103. For example, a brace 101 can function as a power supply and supply operating electricity to other braces via wire 103. In an alternate configuration, power supply 114 is contained external to brace 101 (e.g., in a battery pack attached to a molar) and power is transferred from power supply 114 to brace 101 through wire 103 and wire connector 106.

Figure 2A:
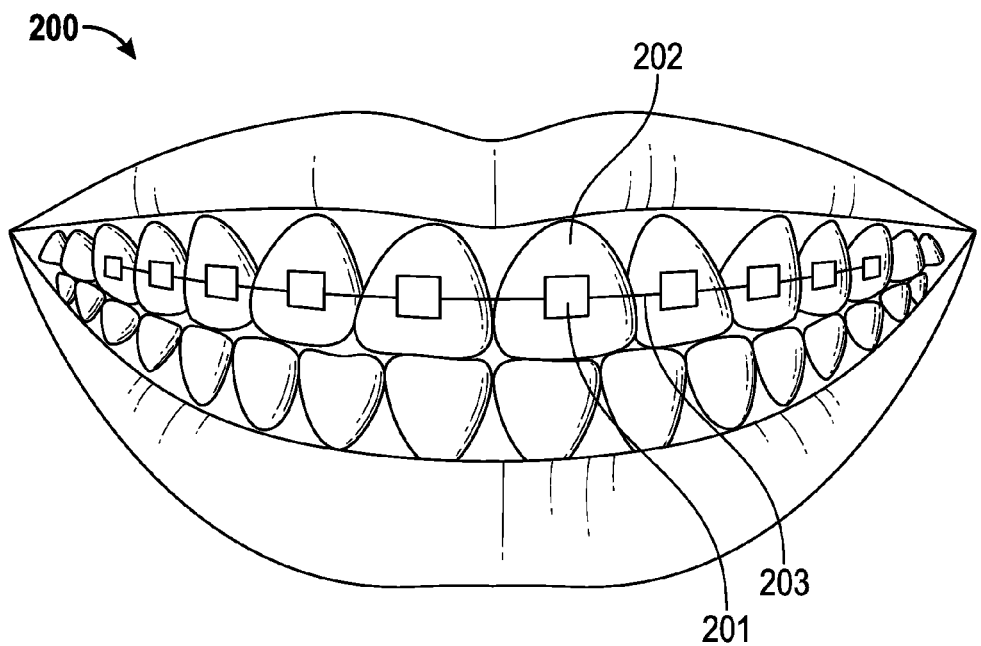
FIG. 2A is a perspective view of an illuminated dental braces system according to another exemplary embodiment.

Referring to FIG. 2A, a schematic view of an illuminated dental braces system 200 is shown according to an exemplary embodiment. System 200 includes braces 201 mounted on teeth 202. Braces 201 are connected through wire 203. System 200 is similar to system 100 in that braces 201 emit light under certain circumstances. However, system 200 achieves a lighting effect through the use of wire 203, which is illuminated. Braces 201 are attached to teeth 202 through specialized dental glue. In an alternative arrangement, braces 201 are secured to teeth 202 via metal rings that wraps around teeth 202 in addition to the dental glue. Wire 203 may be positioned, bent, and tensioned to apply forces to brace 201 in order to move teeth 202 into a designated position and orientation.

Figure 2B:
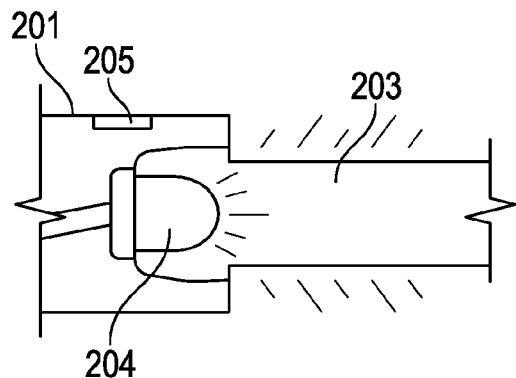
FIG. 2B is a cross-sectional view of an illuminated brace according to the exemplary embodiment of FIG. 2A.

Referring to FIG. 2B, a cross-sectional view of brace 201 is shown according to an exemplary embodiment. Brace 201 includes light source 204. Light source 204 is configured to emit light such that wire 203 appears illuminated when light source 204 is activated. Wire 203 includes a dielectric coating at least partially surrounding a metal core. The dielectric coating can comprise an optical waveguide, such as an optical fiber, configured to emit light from its end or its sides. Light source 204 may be an LED, an OLED, a quantum dot, an incandescent bulb, or any other light source. Light source 204 may include multiple light sources (e.g., an array of LEDs, an array of OLEDs, an array of quantum dots, etc.). Light source 204 may emit a single color of light. Alternatively, light source 204 may be color adjustable such that the color of light emitted by light source 204 is selectable (e.g., white, blue, red, yellow, green, etc.). Alternatively, light source 204 may be capable of emitting multiple different colors of light at the same time. In another alternate configuration, brace 201 comprises multiple housings each having a light source, wherein each of the multiple housings is configured to emit a light having a different color than another housing. In yet another alternative configuration, light source 204 may emit ultraviolet light. Light source 204 may be intensity adjustable such that the intensity of emitted light (i.e., the brightness level of light source 204) is adjustable.

As shown in FIG. 2B, brace 201 includes sensor 205. Sensor 205 is configured to detect a characteristic from its placement within the user's mouth. Sensor 205 detects a characteristic or condition within the user's mouth or outside of the user's mouth. Sensor 205 may be a bacteria sensor configured to detect the bacteria level in the user's mouth. In such embodiments, sensor 205 outputs a feedback signal to processing circuit 210, which may control (e.g., activate, deactivate, adjust brightness, adjust color, etc.) light source 204 based on the detected level of bacteria. In the event the detected level of bacteria exceeds a threshold level, light source 204 is either activated or deactivated depending on user programming. The activated light may be an ultraviolet light (to kill the bacteria) or a colored light (to alert the wearer or another that the wearer should brush his or her teeth). In an alternate configuration, sensor 205 is an ambient light sensor. In such a configuration, light source 204 is activated or deactivated based on the detected light level. Further, the level of light output by light source 204 (i.e., the brightness of light source 204) can be adjusted based on the detected ambient light level. For example, in dark ambient light situations, light source 204 may emit a lower intensity of light as it will be more easily visible; whereas in bright ambient light situations, light source 204 may emit light at a higher intensity. In certain bright ambient light situations, light source 204 may be instructed to not light at all as the light will not be easily visible even at a full brightness setting. Further, if the ambient light level falls below a threshold level of light, processing circuit 210 may determine that the user's mouth is closed, in which case light source 204 is turned on or off based on the programming. In yet another alternate configuration, sensor 205 is an optical sensor configured to detect a lighting pattern emitted from a device external to the user's mouth. In another alternate configuration, sensor 205 is a microphone. In such a configuration, light source 204 may be activated, deactivated, and/or adjusted (e.g., in color or in brightness) based on detected sound levels (e.g., activating with a threshold noise level, increasing or decreasing intensity with increasing or decreasing noise level, changing color based on detected noise level, etc.) and/or detected sound patterns (e.g., voice recognition, music recognition, etc.). In another alternate configuration, sensor 205 is a movement sensor. In such a configuration, light source 204 may be activated, deactivated, and/or adjusted (e.g., in color, in brightness) based on detected movement thresholds and patterns. For example, light source 204 may be activated when a chewing motion is detected or other jaw motion is detected. In another alternate configuration, sensor 205 is a chemical sensor configured to detect the presence and amount of designated chemicals within the mouth (e.g., capsaicin, fluoride, etc.). In yet another alternate configuration, brace 201 includes a sensor array having multiple sensors each configured to detect a different characteristic (e.g., bacteria level inside the user's mouth, an amount of ambient light, noise, jaw movement, etc.). In such a configuration, light source 204 is configured to activate, deactivate, and/or change an operating parameter (e.g., intensity or color) based on detected characteristics. For example, light source 105 may be activated to emit ultraviolet light when detected bacteria levels exceed a threshold amount and when the wearer's mouth is closed based on feedback from the sensor array.

In some arrangements, system 200 may include a chemical secretor. The chemical secretor may be built into each brace 201 or may be built into a non-lighted brace (e.g., a molar brace). Accordingly, brace 201 may include a chemical storage unit (e.g., a tank) and a secretion device (e.g., a sprayer, a nozzle, an outlet). Each brace 201 may include a plurality of secretion devices. The chemical may be any of an anti-bacterial agent, an anti-carcinogenic agent, an oral cleaner (e.g., mouthwash), a breath freshener (e.g., mint spray), or another suitable chemical. The chemical may be secreted from brace 201 in response to a detected bacteria level. For example, if sensor 205 indicates that the detected bacteria level is above a threshold level, the chemical secretor may be programmed to secrete a chemical or combination of chemicals to counter the high bacteria level (e.g., secrete an anti-bacterial agent, a breath freshener, a oral cleaner, or a combination thereof). The chemical secretor may be programmed to secrete the chemical only when the wearer's mouth is closed.

Figure 2C:
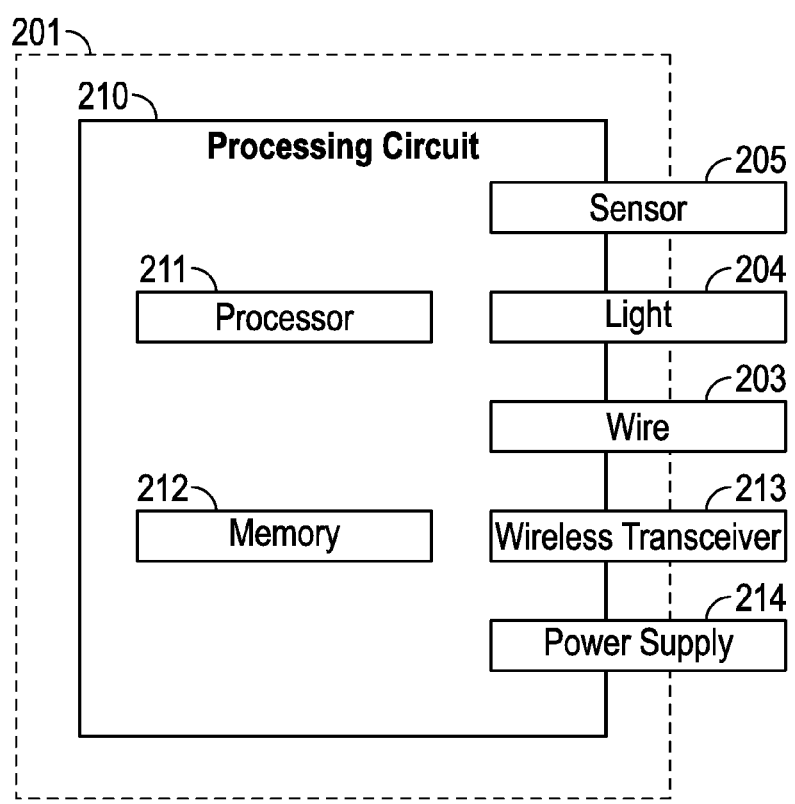
FIG. 2C is a block diagram of a processing circuit of the illuminated brace according to an exemplary embodiment.

In an exemplary embodiment, brace 201 includes processing circuit 210. Referring to FIG. 2C, a block diagram of processing circuit 210 is shown. Processing circuit 210 includes processor 211 and memory 212. Processing circuit 210 communicates with, and is operatively coupled to, light source 204, wire 203, sensor 205, and wireless transceiver 213. Processing circuit 210 is powered by power supply 214. Memory 212 stores necessary programming modules that, when executed by processor 211, control the operation of brace 201 (i.e., control the lighting of brace 201) based on desired user settings and output from sensor 205. For example, memory 212 may include a speech to text conversion module that, when executed by processor 211, converts detected audio patterns into text to be displayed by light source 204 (e.g., with a coded light pattern). By way of further example, memory 212 may include a speech to text conversion module that, when executed by processor 211, identifies words within the detected audio patterns, compares them to one or more stored words, and controls the output of light source 204 based on the comparison, e.g., displaying specified light colors for selected key words. Accordingly, processor 211 is configured to control the output of light source 204, including activating and deactivating light source 204, changing a color of light source 204, changing a brightness level of light source 204, or changing a lighting pattern emitted from a plurality of light sources 204. A user may provide brace 201 settings through an external computing device (e.g., a laptop, a PDA, a smartphone, a tablet, etc.) in communication with processing circuit 210 through wireless transceiver 213. Wireless transceiver 213 is configured to receive and transmit data through a standard wireless networking protocol (e.g., Bluetooth, 802.11, 802.15, Wi-Fi, etc.). Alternatively, wireless transceiver 213 is configured to receive and transmit data through ultrasound or infrared communications. Processing circuit 210 is further configured to communicate with other braces. For example, a first brace 201 can communicate with a second brace 201 such that each light source 204 activates, deactivates, or adjusts such that all lights on connected braces emit light at the same time or at offset times, with the same or different intensities, and/or with the same or different colors to form patterns. Accordingly, brace 201 can communicate with other braces through wireless transceiver 213. Further, brace 201 can communicate with other braces through wire 203 (similar to wire 103, wire 203 can facilitate data and power transfer between connected braces). Processing circuit 210 is further configured to receive lighting instructions from external computing devices through wireless transceiver 213. The received instructions may include an on-demand lighting pattern to be executed by processor 211 upon receipt of the instruction (e.g., a lighting score) or a lighting pattern to be executed by processor 211 upon the detection of a condition or characteristic.

Power supply 214 provides power to brace 201. Power supply 214 may receive power from any suitable source (e.g., a rechargeable battery, a non-rechargeable battery, etc.). In addition to a stand-alone power source such as a battery, power supply 214 may receive operating power and/or charge batteries through wireless inductive power (i.e., by passing radio waves over coils that convert the electro-magnetic energy into electrical energy), by converting mechanical energy present during jaw movement into electrical energy through a mechanical energy converter, by converting solar energy into electrical energy through the use of a photovoltaic cell located on brace 201, and/or by chemically extracting electrical energy from food located within the user's mouth. Brace 201 is configured to transmit or receive power from power supply 214 to another brace through wire connector 106 and wire 203. For example, a brace 201 can function as a power supply and supply operating electricity to other braces via wire 203. In an alternate configuration, power supply 214 is contained external to brace 201 (e.g., in a battery pack attached to a molar) and power is transferred from power supply 214 to brace 201 through wire 203.

Figure 3A:
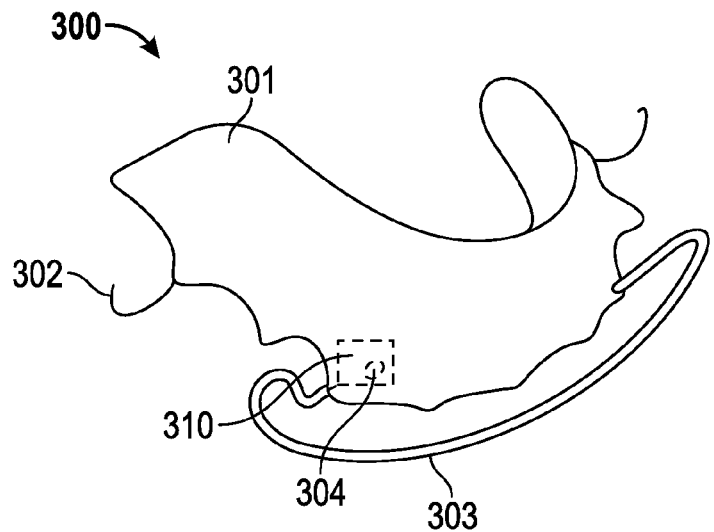
FIG. 3A is a perspective view of an illuminated dental retainer according to an exemplary embodiment.

Referring to FIG. 3A, a schematic view of an illuminated dental retainer system 300 is shown in accordance with an exemplary embodiment. System 300 includes retainer body 301. Retainer body 301 is shaped to fit in a user's mouth and grip the user's teeth with hook 302. Retainer body 301 includes wire 303. Wire 303 is positioned, bent, and tensioned to prevent the user's teeth from shifting and/or to actively shift a user's teeth. Wire 303 is of a similar construction to wire 203 of system 200. Wire 203 is selectively illuminated and carries light emitted from light source 305 (not shown in FIG. 3A). Light source 305 is emits light such that wire 303 appears illuminated when light source 305 is activated. Wire 303 may include a dielectric coating at least partially surrounding a metal core. Light source 305 may be an LED, an OLED, a quantum dot, an incandescent bulb, or any other light source. Light source 305 may include multiple light sources (e.g., an array of LEDs, an array of OLEDs, an array of quantum dots, etc.). Light source 305 is capable of emitting a single color of light. Alternatively, light source 305 is configured to be color adjustable such that the color of light emitted by light source 305 is selectable (e.g., white, blue, red, yellow, green, etc.). Alternatively, light source 305 is capable of emitting multiple different colors of light depending on its programming and activation instructions. In another alternate configuration, retainer body 301 comprises multiple light sources 305, each light source is configured to emit a different color than another light source. In yet another alternative configuration, light source 305 may emit ultraviolet light. Light source 305 is configured to be intensity adjustable such that the intensity of emitted light (i.e., the brightness level of light source 305) is adjustable.

Retainer body 301 serves as a housing for components and includes sensor 304 and processing circuit 310. Sensor 304 can detect a characteristic or condition within the user's mouth or outside of the user's mouth. In one embodiment, sensor 304 is a bacteria sensor configured to detect the bacteria level in the user's mouth. Sensor 304 outputs a feedback signal to processing circuit 310. Processing circuit 310 may activate or deactivate light source 305 based on the detected level of bacteria. In the event the detected level of bacteria exceeds a threshold level, light source 305 is either activated or deactivated depending on user programming. The activated light may be an ultraviolet light (to kill the bacteria) or a colored light (to alert the wearer or another that the wearer should brush his or her teeth). In an alternate configuration, sensor 304 is an ambient light sensor. In such a configuration, light source 305 is activated or deactivated based on the detected light level. Further, the level of light output by light source 305 (i.e., the brightness of light source 305) can be adjusted based on the detected ambient light level. For example, in dark ambient light situations, light source 305 may emit a lower intensity of light as it will be more easily visible; whereas in bright ambient light situations, light source 305 may emit light at a higher intensity. In certain bright ambient light situations, light source 305 may be instructed to not light at all as the light will not be easily visible even at a full brightness setting. Further, if the ambient light level falls below a threshold level of light, processing circuit 310 may determine that the user's mouth is closed, in which case light source 305 is turned either on or off based on the programming. In yet another alternate configuration, sensor 304 is an optical sensor configured to detect a lighting pattern emitted from a device external to the user's mouth. In another alternate configuration, sensor 304 is a microphone.

In such a configuration, light source 305 may be activated, deactivated, and/or adjusted (e.g., in color or in brightness) based on detected sound levels (e.g., activating with a threshold noise level, increasing or decreasing intensity with increasing or decreasing noise level, changing color based on detected noise level, etc.) and/or detected sound patterns (e.g., voice recognition, music recognition, etc.). In another alternate configuration, sensor 304 is a movement sensor. In such a configuration, light source 305 may be activated, deactivated, and/or adjusted (e.g., in color, in brightness) based on detected movement thresholds and patterns. For example, light source 305 may be activated when a chewing motion is detected or other jaw motion is detected. In another alternate configuration, sensor 304 is a chemical sensor configured to detect the presence and amount of designated chemicals within the mouth (e.g., capsaicin, fluoride, etc.). In yet another alternate configuration, retainer body 301 includes a sensor array having multiple sensors each configured to detect a different characteristic (e.g., bacteria level inside the user's mouth, an amount of ambient light, noise, jaw movement, etc.). In such a configuration, light source 305 is configured to activate, deactivate, and/or change an operating parameter (e.g., intensity or color) based on detected characteristics. For example, light source 105 may be activated to emit ultraviolet light when detected bacteria levels exceed a threshold amount and when the wearer's mouth is closed based on feedback from the sensor array.

In some arrangements, retainer body 301 may include a chemical secretor. Accordingly, retainer body 301 includes a chemical storage unit (e.g., a tank) and a secretion device (e.g., a sprayer, a nozzle, an outlet). Retainer body 301 may include a plurality of secretion devices for chemical secretion across the entire area of the wearer's mouth. The chemical may be any of an anti-bacterial agent, an anti-carcinogenic agent, an oral cleaner (e.g., mouthwash), a breath freshener (e.g., mint spray), or another suitable chemical. The chemical may be secreted from retainer body 301 in response to a detected bacteria level. For example, if sensor 304 indicates that the detected bacteria level is above a threshold level, the chemical secretor may be programmed to secrete a chemical or combination of chemicals to counter the high bacteria level (e.g., secrete an anti-bacterial agent, a breath freshener, a oral cleaner, or a combination thereof). The chemical secretor may be programmed to secrete the chemical only when the wearer's mouth is closed.

Figure 3B:
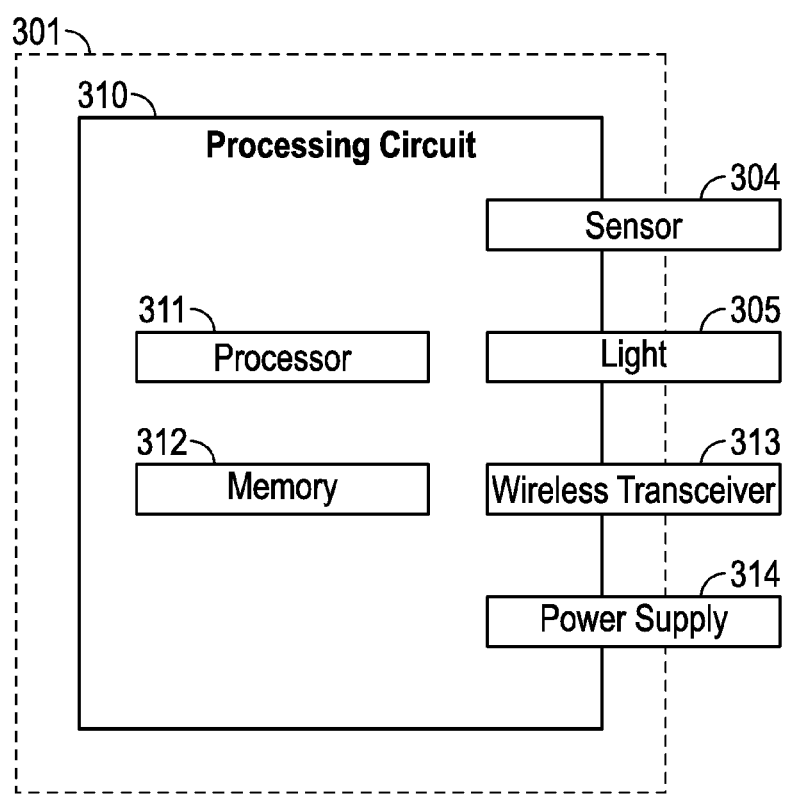
FIG. 3B is a block diagram of a processing circuit of the illuminated dental retainer according to an exemplary embodiment.

In an exemplary embodiment, retainer body 301 includes processing circuit 310. Referring to FIG. 3B, a block diagram of processing circuit 310 is shown. Processing circuit 310 includes processor 311 and memory 312. Processing circuit 310 communicates with, and is operatively coupled to, light source 305, wire 303, sensor 304, and wireless transceiver 313. Processing circuit 310 is powered by power supply 314. Memory 312 stores necessary programming modules that, when executed by processor 311, control the operation of retainer body 301 (i.e., control the lighting of retainer body 301) based on desired user settings and output from sensor 304. For example, memory 312 may include a speech to text conversion module that, when executed by processor 311, converts detected audio patterns into text to be displayed by light source 305 (e.g., with a coded light pattern). By way of additional example, memory 312 may include a speech to text conversion module that, when executed by processor 311, identifies words within the detected audio patterns, compares them to one or more stored words, and controls the output of light source 305 based on the comparison, e.g., displaying specified light colors for selected key words. Accordingly, processor 311 is configured to control the output of light source 305, including activating and deactivating light source 305, changing a color of light source 305, changing a brightness level of light source 305, or changing a lighting pattern emitted from a plurality of light sources 305. A user may provide retainer body 301 settings through an external computing device (e.g., a laptop, a PDA, a smartphone, a tablet, etc.) in communication with processing circuit 310 through wireless transceiver 313. Wireless transceiver 313 is configured to receive and transmit data through a standard wireless networking protocol (e.g., Bluetooth, 802.11, 802.15, Wi-Fi, etc.). Alternatively, wireless transceiver 313 is configured to receive and transmit data through ultrasound or infrared communications. Processing circuit 310 is further configured to communicate with other braces. For example, a first retainer body 301 can communicate with a second retainer body 301 such that each light source 305 contained on each retainer body 301 activate, deactivate, or adjust in sync such that all lights on connected braces emit light at the same time or multiple braces light at different times, with different intensities, and/or with different colors to form patterns. Accordingly, retainer body 301 can communicate with other braces through wireless transceiver 313. Further, retainer body 301 can communicate with other braces through wire 303 (similar to wire 103, wire 303 can facilitate data and power transfer between connected braces). Processing circuit 310 is further configured to receive lighting instructions from external computing devices through wireless transceiver 313. The received instructions may include an on-demand lighting pattern to be executed by processor 311 upon receipt of the instruction (e.g., a lighting score) or a lighting pattern to be executed by processor 311 upon the detection of a condition or characteristic.

Power supply 314 provides power to retainer body 301. Power supply 314 may receive power from any suitable source (e.g., a rechargeable battery, a non-rechargeable battery, etc.). In addition to a stand-alone power source such as a battery, power supply 314 may receive operating power and/or charge batteries through wireless inductive power (i.e., by passing radio waves over coils that convert the electro-magnetic energy into electrical energy), by converting mechanical energy present during jaw movement into electrical energy through a mechanical energy converter, by converting solar energy into electrical energy through the use of a photovoltaic cell located on retainer body 301, and/or by chemically extracting electrical energy from food located within the user's mouth. In an alternate configuration, power supply 314 is contained external to retainer body 301 (e.g., in a battery pack attached to a molar) and power is transferred from power supply 314 to retainer body 301 through wire 303.

As discussed above, processing circuit 110, processing circuit 210, and processing circuit 310 respectively control the lighting of light source 105, light source 204, and light source 305 based on programmed parameters, sensor feedback signals, data received from other lighted dental devices (e.g., through wireless transceiver 113 and/or through wire connector 106, through wireless transceiver 213 and/or wire 203, or through wireless transceiver 313), and/or commands and instructions received from external computing devices. The processing circuits are configured to receive programming parameters and instructions from a user. The programming parameters and instructions indicate when the lights are to be activated, deactivated, and/or adjusted. The user may program parameters and instructions through an interface on an external computing device (e.g., a laptop, a PDA, a smartphone, a tablet, etc.) and upload the parameters and settings to the processing circuit (e.g., processing circuit 110, processing circuit 210, or processing circuit 310) where they are stored in system memory (e.g., memory 112, memory 212, or memory 312).

System 100, system 200, and system 300 are highly programmable by users. A user may program light activation, deactivation, light intensity level, light color, and any combination of any in a lighting parameter (e.g., as a lighting score indicating when the light sources are activated, deactivated, and how the light source operating parameters are changed) based on any number of parameters, including time of day, detected threshold levels from sensors (e.g., detected ambient light, detected noise levels, detected bacteria levels, etc.), detected patterns (e.g., speech patterns, music patterns, jaw motion patterns, etc.), communication with other oral illumination systems, communication with external computing devices, and any combination thereof. Further, the user can program communication settings for each system, both on the micro level (i.e., how individual braces communicate with other braces within the same system) and on the macro level (i.e., how one user's system communicates with another user's system). Each lighted device is programmable with an operating mode such that the lights will activate, deactivate, and adjust without any additional programming from the user.

Figure 4:
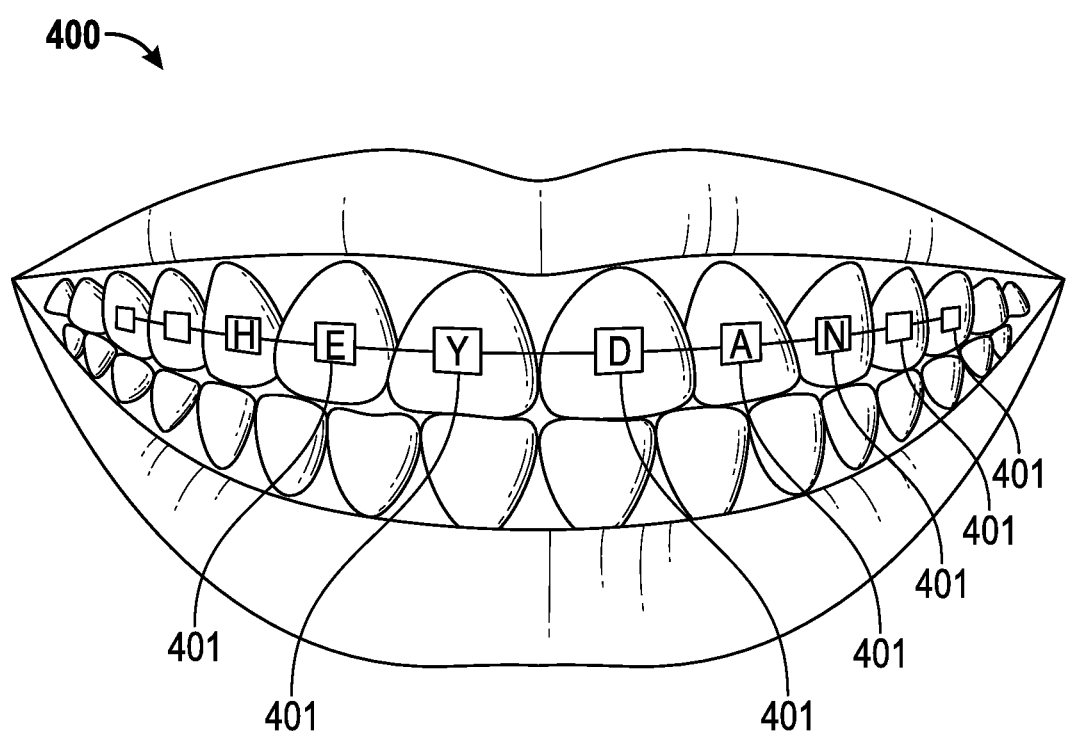
FIG. 4 is a perspective view of an illuminated braces system displaying a message according to an exemplary embodiment.

System 100, system 200, and system 300 are programmable to display messages upon a trigger event or command by the user. The trigger events may be programmed by the user or be part of a default setting. The trigger events may include any detected sensor statuses (e.g., detected ambient light, detected noise levels, detected bacteria levels, detected food characteristic etc.), detected patterns (e.g., vocal speech patterns, music patterns, jaw motion patterns, etc.), communication with other devices, and any combination thereof. The messages are displayed in a format such that other people can read the messages. The messages are displayed with a pattern of light pulses representing coded words (e.g., Morse code), a pattern of color changes representing coded words, or a combination of pulses and color changes. In systems including a display or light array capable of displaying characters and numerals, the message can be displayed in text characters and numerals displayed on the display units or light arrays. For example, referring to FIG. 4, an exemplary lighted braces system 400 is shown as displaying the phrase "HEY DAN" across displays integrated into braces 401.

The text of the message can be preprogrammed in conjunction with the programmed triggering event. For example, the user can program an oral illumination system (e.g., system 100) to display the word "SPICY" when the user eats food having a threshold level of capsaicin or a food having a threshold number of Scoville units. Accordingly, when the user eats spicy food exceeding the set threshold level, a system sensor (e.g., sensor 107) indicates that the user is eating food exceeding the threshold, and the word SPICY is displayed across the system displays. Alternatively, the text of the message is automatically provided by the triggering event. For example, a user may indicate that the user's speech is to be transcribed. Accordingly, when the user speaks, an audio sensor (e.g., sensor 107) provides a feedback signal of the user's speech, which is converted to text by a system processor (e.g., processor 111), and the words are displayed across the system displays. The words may scroll (e.g., like a ticker) across the braces or appear and disappear as the words are spoken. In yet another alternative arrangement, the text of the message is sent from an external computing device. In such an arrangement, a user programs a message into an external computing device (e.g., laptop, tablet, PDA, smartphone, etc.), and the message is transmitted to the system and received by a wireless transceiver (e.g., wireless transceiver 113, wireless transceiver 213, or wireless transceiver 313). Once the message is received by the system, it is processed and displayed. The message need not be transmitted by the wearer of the system. For example, a user can configure a data link to a radio station, an internet music streamer (e.g., Pandora®, Slacker®, etc.), a personal audio player (e.g., iPod®, Zune®, etc.), or another external system configured to transmit musical lyrics or text to be displayed to be displayed in synchronization with the music being played. In another alternative arrangement, multiple units can transmit and receive messages to be displayed to each other through their respective wireless transceivers (e.g., wireless transceiver 113, wireless transceiver 213, or wireless transceiver 313) or through onboard optical sensors that detect a lighting pattern external to the wearer's system (e.g., from another user's system). In such an arrangement, messages being displayed on a first unit can be displayed on a second unit located within a transmission distance. The messages or light patterns can be reproduced in phase (simultaneously) or out of phase (at a designated timing offset) and having the same or altering coloring, time sequencing, spatial patterning, and/or illumination level to the messages being displayed on the transmitting unit. Alternatively, a complementary lighting pattern can be displayed in response to a detected external lighting pattern.

System 100, system 200, and system 300 may be programmed to display messages, colors, and/or symbols based upon the detected emotional state of the user. In such an embodiment, system 100, system 200, and system 300 may utilize audio sensors to analyze parameters of a user's speech, including the tone of voice, pitch, the speed of the speech, rhythm, the duration of pauses, the energy of the voice signal, and other speech parameters. System 100, system 200, and system 300 then process the identified parameters and match the parameters with emotions. System 100, system 200, and system 300 can use the parameters to identify user anger, happiness, boredom, doubtfulness, depression, stress, romantic inclinations, romantic receptiveness, confidence, confusion, hopefulness, jealousy, disappointment, frustration, surprise, tiredness, embarrassment, etc. Sensors in addition to audio sensors may be used to supplement the emotion identification process (e.g., blood pressure sensor, heart rate sensor, etc.). The lighting pattern in response to the detected emotional state indicates the emotional state of the user. For example, if a user is angry, the light may be programmed to pulse red. If the user is happy, the light may be programmed to pulse green.

Any of the above discussed displayed messages or statuses may be represented with a pattern of light pulses representing coded words (e.g., Morse code), a pattern of color changes representing coded words, a combination of pulses and color changes, and/or with displayed text and symbols.

In an exemplary embodiment, system 100, system 200, and system 300 may be configured to store usage statistics and transmit reports to external computing devices. The usage statistics may relate to any of displayed text, displayed characters, displayed lighting patterns, detected activities (e.g., brushing teeth, eating food), detected sensor statuses (e.g., bacterial levels, emotions, etc.), and communication with other systems. The statistics are maintained in a log that is stored in system memory (e.g., memory 112, memory 212, and memory 312). The statistics can be uploaded to an external computing device on demand (e.g., by indicating the statistics that are to be uploaded through a user interface on the external computing device) or are automatically uploaded to an external computing device on a regular basis (e.g., every night, once a week, etc.). Further, a user can receive alerts for detected events or non-events. For example, if a child is wearing any of system 100, system 200, or system 300, the child's parent may program alerts indicating that the child brushed his teeth or if the child doesn't brush his teeth for a designated period of time. The alert may be sent via email, SMS, and/or to a system user interface (e.g., a system webpage, a push notification for a system smartphone application, etc.).

Figure 5:
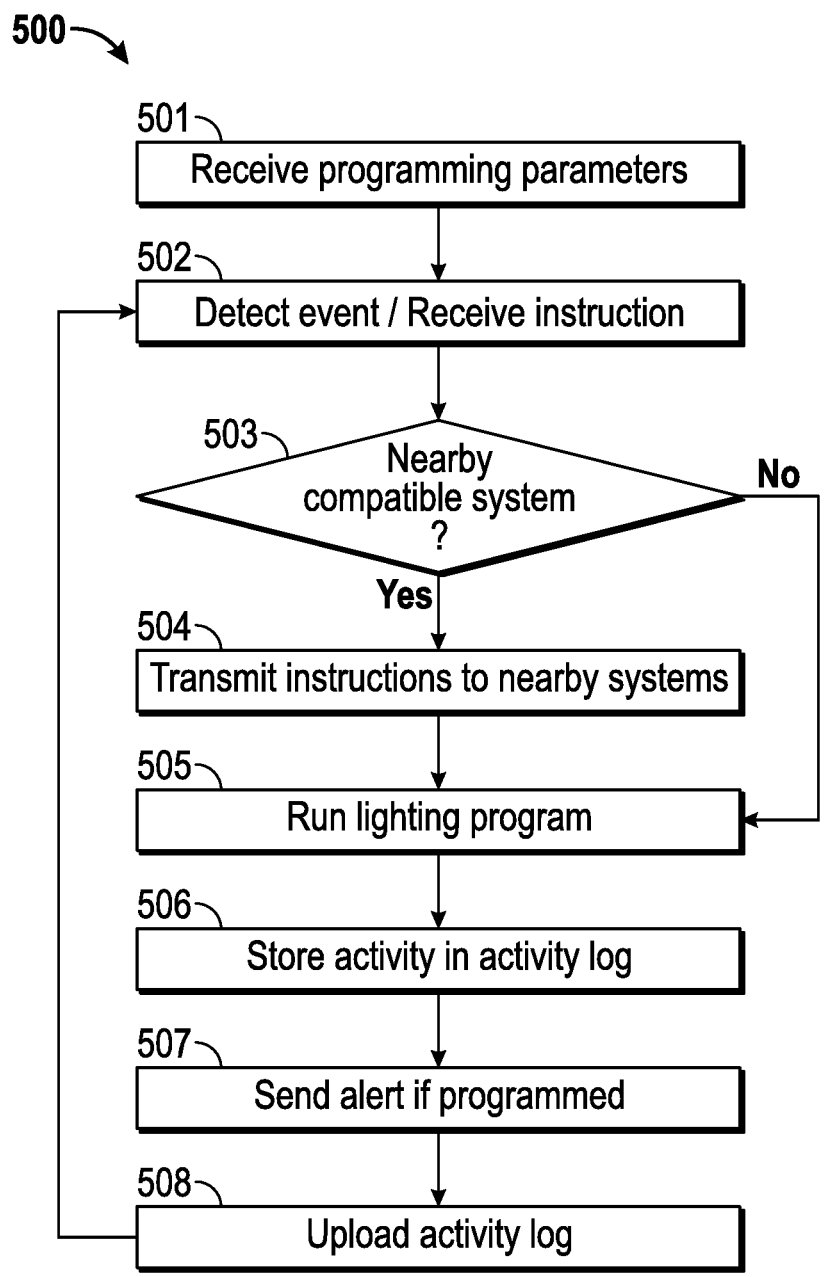
FIG. 5 is a flow diagram describing a method of illuminating an oral illumination system according to an exemplary embodiment.

Referring to FIG. 5, a method 500 of executing a lighting program on a lighting system based on a detected event or received instruction is shown according to an exemplary embodiment. Method 500 may be used with system 100, system 200, system 300, or another similar system configured to run a lighting program based on detected conditions or received instructions. Prior to the execution of a lighting program, the system receives programming parameters (step 501). The programming parameters include a trigger event. The programmed trigger events may pertain to a time of day, detected threshold levels from sensors onboard the system (e.g., detected ambient light, detected noise levels, detected bacteria levels, detected speech, detected ambient noise patterns, jaw movement, detected chemical presence, system movement, etc.), a detected status (e.g., emotion, verbal communication, etc.), instructions received from external computing devices and systems, and any combination thereof. The programming parameters also include communication preferences pertaining to if and how a system is to communicate with other lighting systems within a communication range. The programming parameters also include activity log preferences (e.g., what system events and activities are stored in an activity log, how often the activity log is uploaded to an external computing devices, etc.). The programming parameters may further include alert preferences. A user can configure different types of alerts (e.g., SMS, e-mail, smartphone push notifications, social media postings, etc.) based on different detected events and executed lighting programs. The programming parameters are sent to the system from an external computing device (e.g., laptop, PDA, smartphone, tablet, etc.). A user of the system provides the parameters through interaction with a system user interface presented on the external computing device. The programming parameters are received by the system through a wireless transceiver of the system and stored in system memory.

Referring to FIG. 5, after the system is programmed, the system waits until an event is detected or an instruction is received (step 502). The system includes at least one sensor. The sensor is any of a bacteria sensor, an ambient light sensor, a microphone, a movement sensor, a chemical sensor, a heart rate sensor, a blood pressure sensor, or another sensor. The sensor is configured to provide a feedback signal of detect events and thresholds (e.g., ambient light, noise levels, bacteria levels, speech, ambient noise patterns, jaw movement, system movement, food composition, chemical presence, blood pressure, heart rate, etc.) to a system processor. The system processor determines if a trigger event has occurred based on the sensor feedback.

Further, the system is configured to receive lighting instructions. The lighting instructions may come from an external computing device (e.g., laptop, PDA, smartphone, tablet, etc.). The user can indicate a lighting program to be executed by the system processor through interaction with a system user interface presented on the external computing device. The instruction may include the lighting program (e.g., a lighting score) or the instruction may indicate that the processor is to execute a lighting program already stored in the system's memory. The instruction further indicates whether the lighting program is to be executed upon receipt of the instruction, upon the detection of a characteristic, or after a delay (e.g., a set time delay or a designated date and time). The lighting instructions are received by the system through a wireless transceiver of the system. Alternatively, the system receives lighting instructions from another system. In such an arrangement, an event is detected or an on-demand lighting instruction is received at a remote system (e.g., another user's system 100, system 200, or system 300), and the remote system transmits a lighting instruction to the system. The lighting instruction is received through the wireless transceiver of the system. In yet another alternative arrangement, the system includes an optical sensor that detects when a remote system (e.g., another user's system 100, system 200, or system 300) is executing a lighting program through visually detecting the lighting program. In such an arrangement, the processor of the system determines what lighting program is being executed and can instruct execution of the same or a complimentary lighting program on the system.

Further referring to FIG. 5, the system determines if there is a nearby compatible system within communication range (step 503). Multiple systems communicate with each other if permitted by the programming parameters provided in step 501. If programmed to do so, upon the detection of an event or receipt of an instruction in step 502, the system searches for nearby compatible lighting systems. The nearby compatible lighting system may be within a communication distance (e.g., such that the wireless transceivers of the systems can exchange data). If a nearby compatible lighting system is located, the system transmits a lighting program instruction to the nearby system (step 504). Alternatively, the systems do not need to be within a communication distance and a server can relay commands through a network (e.g., the Internet) from one system to another regardless of the physical distance between the two systems. In yet another alternative, the system determines that a lighting pattern is currently being executed through the use of an optical sensor that detects an external lighting pattern.

After instructions are sent to nearby compatible lighting systems, or if no nearby compatible lighting systems have been identified, the system's processor executes the lighting program (step 505). The lighting program may include a pattern of light pulses, a pattern of color changes, or a combination of light pulses and color changes. The pattern may be an artistic pattern or a coded lighting pattern representing a coded message to a third party (e.g., a lighting pattern of pulses of light from the light, a pattern utilizing Morse code to display a message, a pattern of different colors displayed by the light, etc.). In some configurations, the system includes a display or a light array capable of displaying characters, numerals, and symbols. In such an arrangement, the lighting program can include specific letters, characters, numerals, and symbols that are displayed on the display units or light arrays. The letters and characters may scroll (e.g., like a ticker) across the system displays or appear and disappear. Accordingly, the system activates, deactivates, and controls the light source in accordance with the lighting program to be executed.

Further referring to FIG. 5, the system creates an entry in a system activity log detailing the lighting program's execution (step 506). The activity log is stored in the memory of the system. The entry in the activity log includes a description of the activity (e.g., a description of the triggering event or received instruction, the name of the lighting program executed, a description of the lighting program's light sequence and color sequence, etc.), the time of the activity, and whether any instructions were sent or received from nearby systems. The entry is stored in a memory of the system (e.g., memory 112, memory 212, or memory 312).

If the user provided programmed alerts during step 501, the system initiates an alert based on the detected event and/or the executed lighting program (step 507). As indicated above, a user can configure different types of alert preferences (e.g., SMS, e-mail, smartphone push notifications, social media postings, etc.) based on different detected events and executed lighting programs. First, the system formats an alert in accordance to the alert preferences. The alert is formatted to include a description of the detected event, characteristic, or the received instruction, including the time and date of the event. Further, the alert may include a description of the executed lighting program. The alert is then transmitted via the user selected alert channel (SMS, e-mail, smartphone push notification, social media posting, etc.). The system initiates the transmission of the alert through the system's wireless transceiver. Depending on the type of alert channel selected by the user, the system may forward the alert to a third-party alert service (e.g., a cellular carrier for SMS delivery, a social media server for social media integration, etc.). The system updates the activity log to include an indication that an alert was sent, including the time of the alert and the alert message.

The system is configured to upload the activity log to an external computing device (step 508). The external computing device may be a user operated device (e.g., a laptop, a PDA, a smartphone, a tablet, etc.) or a system affiliated device (e.g., a system server, where the activity log is stored for later access by a user). The activity log upload may be uploaded based upon a predetermined upload schedule (e.g., every hour, every day, every other day, once a week, once a month, etc.). Alternatively, the activity log may be uploaded after each detected event or received instruction. In yet another alternative arrangement, the activity log may be uploaded on-demand based on a user command received from an external computing device. In such an arrangement, the user can initiate an on-demand upload of the activity log even if the activity log is scheduled to later be automatically uploaded according to a predetermined schedule. After initial setup, the system remains in an event detection mode or an instruction receiving mode and the method repeats for each detected event or received instruction.

Figure 6:
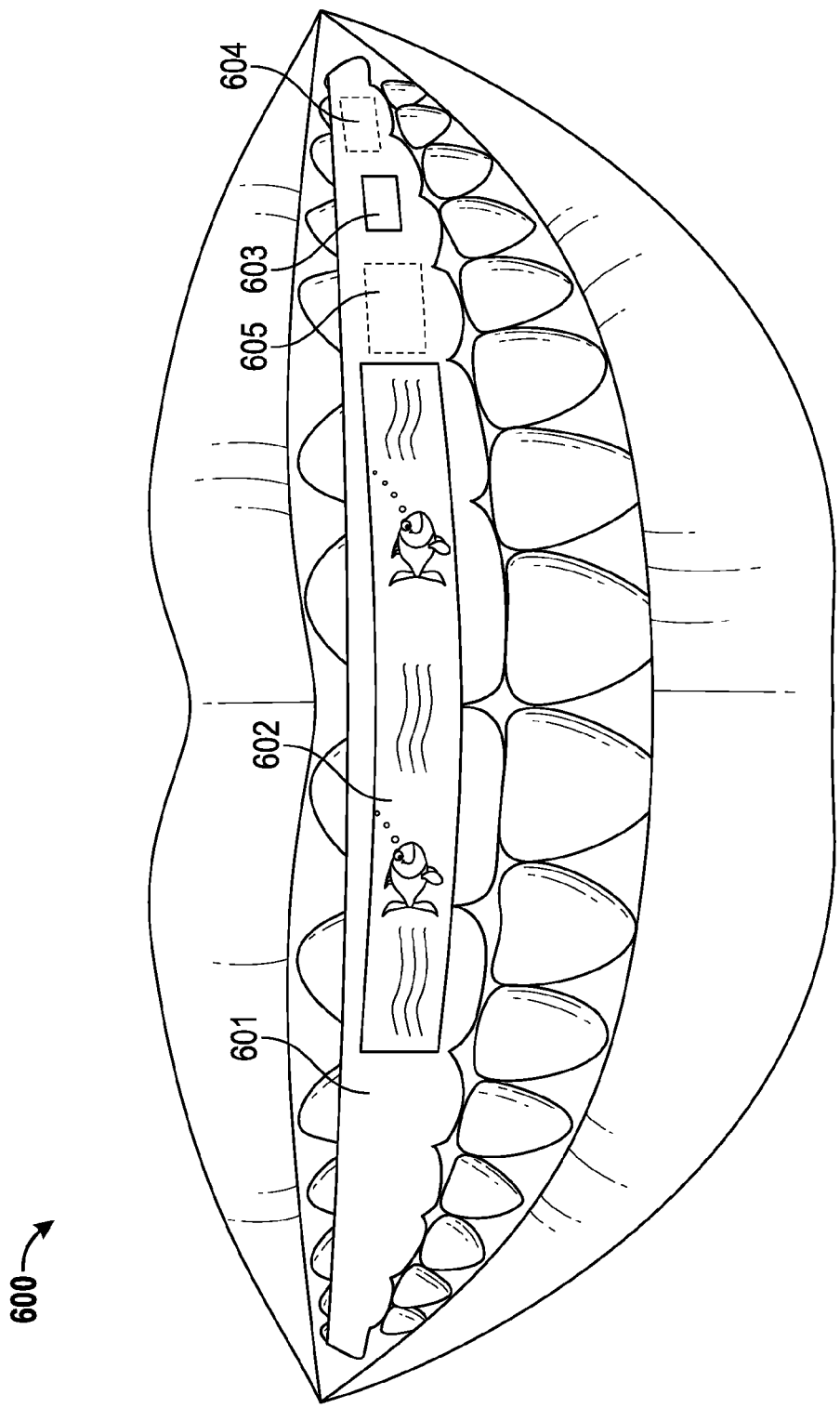
FIG. 6 is a perspective view of an oral device having a display according to an exemplary embodiment.

Referring to FIG. 6, an oral system 600 is shown according to an exemplary embodiment. System 600 includes body 601. Body 601 may be a mouth guard, an oral retainer (e.g., configured to prevent relative movement of one tooth with respect to another tooth when worn), an orthodontic treatment device (e.g., configured to shift one tooth relative to another tooth when worn), or another oral device. Body 601 is configured to be coupled to a structure in the wearer's mouth. For example, body 601 may be configured to mount on a wearer's upper set of teeth, lower set of teeth, or both. For example, body 601 may be sized and shaped as a tray to fit over the wearer's teeth. When worn by a wearer, body 601 at least partially covers a plurality of the wearer's teeth. Body 601 may be constructed out of a semi-rigid plastic. System 600 includes display 602 coupled to body 601. Display 602 may be an LCD display, an LED display, an OLED display, a TFT display, a quantum dot display, a plasma display, or another suitable type of display. Display 602 may be capable of displaying a static image or a video image. Display 602 may be curved to follow the curvature of the wearer's mouth or the curvature of body 601. System 600 includes sensor 603. Sensor 603 may be any of the sensors described above with respect to systems 100, 200, 300, and/or 400.

System 600 further includes power supply 604. Power supply 604 provides power to system 600. Power supply 604 may receive power from any suitable source (e.g., a rechargeable battery, a non-rechargeable battery, etc.). In addition to a stand-alone power source such as a battery, power supply 604 may receive operating power and/or charge batteries from a wireless inductive power generator (i.e., by passing waves over coils that convert the electro-magnetic energy into electrical energy), by converting mechanical energy present during jaw movement into electrical energy through a mechanical energy converter, by converting solar energy into electrical energy through the use of a photovoltaic cell located on body 601, and/or by chemically extracting electrical energy from food located within the user's mouth. In an alternate configuration, power supply 604 is contained external to body 601 (e.g., in a battery pack attached to a molar) and power is transferred from power supply 604 to system 600 through a connecting wire.

System 600 further includes controller 605. Controller 605 controls display 602 based on sensor 603 feedback. Controller 605 may be programmed to activate, deactivate, change images, change colors, and/or change brightness of display 602. Controller 605 may be programmed in a similar manner to processing circuit 210 of system 200 and processing circuit 310 of system 300 such that controller 605 controls system 600 in a similar manner as processing circuit 210 controls system 200 and processing circuit 310 controls system 300.

The above described illuminated braces (e.g., brace 101 and brace 201) are not limited for use on teeth as lighted oral braces configured to reposition teeth. An individual brace (e.g., brace 101 or brace 201) or a grouping of braces may be mounted to a tooth overlay, dentures, dental crowns, dental retainers, dental implants, and mouth guards. Alternatively, operative components (i.e., lights, sensors, processing circuits, power sources, wires, etc.) may be integrated into tooth overlays, dentures, dental crowns, dental retainers, dental implants, and mouth guards such that lighting, sensing, and processing components are integrated into the dental structures. Still further, brace 101 may be mounted to objects and body parts other than the mouth. For example, brace 101 may be mounted to fingernails, jewelry, clothing, shoes, accessories, cups, mugs, dishes, desks, etc. The above described lighted wires (e.g., wire 203 and wire 303 may also be incorporated into non-dental uses).

The construction and arrangement of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. The elements and/or assemblies of the enclosure may be constructed from any of a wide variety of materials that provide sufficient strength or durability, and in any of a wide variety of colors, textures, and combinations. Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word "exemplary" is intended to present concepts in a concrete manner. Accordingly, all such modifications are intended to be included within the scope of the present inventions. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the spirit of the appended claims.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps, and decision steps.

What is claimed:

1. An orthodontic apparatus having an oral illumination feature and configured for placement in a mouth, comprising:
    a housing configured to be coupled to a structure in the mouth, the housing including a processing circuit;
    a sensor coupled to the housing and configured to detect a characteristic from within the mouth, wherein the sensor provides a feedback signal indicative of the characteristic to the processing circuit, wherein the sensor is a microphone and the characteristic is a noise;
    a light source coupled to the housing and operatively coupled to the processing circuit; and
    a power source coupled to the housing;

wherein the processing circuit is configured to:
identify a sound pattern based on the feedback signal,
identify a word from the sound pattern,
compare the indentified word to a list of stored words, and
control the light source based upon the result of the comparison.

2. The apparatus of claim 1, wherein the processing circuit changes a color of the light source in response to the feedback signal.

3. The apparatus of claim 1, wherein the processing circuit changes a brightness level of the light source in response to the feedback signal.

4. The apparatus of claim 1, wherein the processing circuit activates the light source in response to the feedback signal.

5. The apparatus of claim 1, wherein the processing circuit activates the light source when the noise exceeds a threshold noise level.

6. The apparatus of claim 1, wherein the light source comprises a display capable of displaying a text character or a symbol.

7. The apparatus of claim 6, further comprising a speech to text conversion module stored in a memory of the processing circuit, wherein at least a portion of a detected word is displayed on the display.

8. The apparatus of claim 1, wherein the housing is part of a dental brace configured to reposition a tooth within the mouth.

9. The apparatus of claim 8, further comprising a wire connector coupled to the housing.

10. The apparatus of claim 8, further comprising a wire coupled to the housing, wherein the wire is configured to attach to a second dental brace configured to reposition a second tooth within the mouth.

11. The apparatus of claim 10, wherein the wire is illuminated by the light source.

12. An orthodontic apparatus having an oral illumination feature and configured for placement in a mouth, comprising:
a housing configured to be coupled to a structure in the mouth, the housing including a processing circuit;
a wireless receiver coupled to the housing and operatively coupled to the processing circuit;
a light source coupled to the housing and operatively coupled to the processing circuit;
a power source coupled to the housing; and
a sensor coupled to the housing and configured to detect a characteristic from within the mouth, wherein the sensor provides a feedback signal indicative of the characteristic to the processing circuit, wherein the sensor is a microphone and the characteristic is a noise;
wherein the processing circuit is configured to control the light source in response to an instruction received through the wireless receiver.

13. The apparatus of claim 12, wherein the instruction comprises a light source activation instruction.

14. The apparatus of claim 12, wherein the instruction comprises a light source deactivation instruction.

15. The apparatus of claim 12, wherein the instruction comprises an instruction to implement a stored lighting pattern.

16. The apparatus of claim 12, wherein the instruction includes a lighting pattern to be executed by the processing circuit when the instruction is received.

17. The apparatus of claim 12, wherein the instruction includes a detected condition and a lighting pattern to be executed by the processing circuit when the detected condition corresponds to the characteristic.

18. The apparatus of claim 12, wherein the processing circuit identifies a sound pattern of the noise as vocal speech or music.

19. The apparatus of claim 12, wherein the light source includes a display capable of displaying a text character or a symbol.

20. The apparatus of claim 19, further comprising a speech to text conversion module stored in the memory, wherein at least a portion of a detected word is displayed on the display.

21. The apparatus of claim 12, wherein the housing is part of a dental brace configured to reposition a tooth.

22. The apparatus of claim 21, further comprising a wire connector coupled to the housing.

23. The apparatus of claim 22, further comprising a wire coupled to the wire connector, wherein the wire comprises an optical waveguide, configured to emit light from a side or end of the waveguide.

24. An orthodontic apparatus having an oral illumination feature and configured for placement in a mouth, comprising:
a housing configured to be coupled to a structure in the mouth, the housing including a processing circuit;
a sensor coupled to the housing and configured to detect a characteristic from within the mouth, wherein the sensor provides a feedback signal indicative of the characteristic to the processing circuit, wherein the sensor is a microphone and the characteristic is a noise;
a light source coupled to the housing and operatively coupled to the processing circuit, wherein the light source comprises a display capable of displaying a text character or a symbol;
a speech to text conversion module stored in a memory of the processing circuit; and
a power source coupled to the housing;
wherein the processing circuit is configured to:
identify a sound pattern based on the feedback signal,
control the light source in response to the feedback signal, wherein at least a portion of a detected word in the sound pattern is displayed on the display.

* * * * *